US005863721A

United States Patent [19]
Gilson et al.

[11] Patent Number: 5,863,721
[45] Date of Patent: Jan. 26, 1999

[54] BACTERIAL DIAGNOSTIC PROBE

[75] Inventors: Eric Gilson; Jean-Marie Clement; David Perrin; Agnes Ullmann; Maurice Hofnung, all of Paris, France

[73] Assignee: Institut Pasteur, Paris, France

[21] Appl. No.: 478,854

[22] Filed: Jun. 7, 1995

Related U.S. Application Data

[63] Continuation of Ser. No. 164,769, Dec. 10, 1993, Pat. No. 5,492,811, which is a continuation of Ser. No. 984,289, Dec. 1, 1992, abandoned, which is a continuation of Ser. No. 870,234, Apr. 20, 1992, abandoned, which is a continuation of Ser. No. 602,914, Oct. 24, 1990, abandoned, which is a continuation of Ser. No. 085,178, Aug. 14, 1987, abandoned.

[51] Int. Cl.$^6$ ..................................................... C12Q 1/68
[52] U.S. Cl. ................................................................... 435/6
[58] Field of Search ............................... 435/6; 536/23.5, 536/23.1, 24.1, 24.3, 24.33, 25.6

[56] References Cited

U.S. PATENT DOCUMENTS

| | | | |
|---|---|---|---|
| 4,342,833 | 8/1982 | Chirikjian | 435/178 |
| 4,358,535 | 11/1982 | Falkow et al. | 435/5 |
| 4,801,530 | 1/1989 | Nogueira et al. | 435/6 |
| 5,288,611 | 2/1994 | Kohne | 435/6 |
| 5,492,811 | 2/1996 | Gilson et al. | 435/6 |

FOREIGN PATENT DOCUMENTS

| | | |
|---|---|---|
| 0252558A2 | 1/1988 | European Pat. Off. |
| 2823573 | 12/1978 | Germany |
| WO 84/01174 | 3/1984 | WIPO |
| WO 87/05907 | 10/1987 | WIPO |

OTHER PUBLICATIONS

Bachellier et al., "Bacterial interspersed mosaic elements (BIMEs) are present in the genome of *Klebsiella*," Mol. Microbiol. 7(4):537–544 (1993).

Britten et al., "Hybridisation Strategy," Nucleic Acid Hybridisation: A Practical Approach, 1–15 (Hames et al., eds. IRL Press Limited, Oxford, England, pp. 3–15, 1986).

Correia et al., A 26–Base–Pair Repetitive Sequence Specific for *Neisseria gonorrhoeae* and *Neisseria meningitidis* Genomic DNA, J. Bacteriol. 167(3):1009–1015 (1986).

Enea, V., "Sensitive and Specific DNA Probe for Detection of *Plasmodium falciparum*," Mol. & Cell. Biol. 6(1):321–324 (1986).

Gilson et al., "A family of dispersed repetitive extragenic palindromic DNA sequences in *E. coli*," Embo J. 3(6):1417–1421 (1984).

Gilson et al., "A Subfamily of *E. coli* Polindromic Units Implicated in Transcription Termination?," Ann. Inst. Pasteur/Microbiol. 137B: 259–270 (1986).

Gilson et al., "Palindromic units from *E. coli* as binding sites for a chromoid–associated protein," FEBS 206(2):323–328 (1986).

Gilson et al., "Structure and Function of a Family of Procaryotic Repetitive Sequences: The Palindromic Unit," FEBS Advanced Course on Genome Organization and Evolution, Abstract, Sep. 1–6, 1986.

Gilson et al., "Species Specificity of Bacterial Palindromic Units," J. Mol. Evol. 25:371–373 (1987).

Gilson et al., "Palindromic units: a case of highly repetitive DNA sequences in bacteria," TIG 3(8):226–230 (1987).

Higgins et al., "A novel intercistronic regulatory element of prokaryotic operons," Nature 298:760–762 (1982).

Kloos et al., "The Biochemical and Genetic Characterization of '*Bordetella pertussis*'," PB81–140147, NTIS (Dec. 1980).

Mattei et al., "Cloning of a Coding Sequence of *Bordetella Pertussis* Filamentous Hemagglutinin Gene," bacterial Vaccines and Local Immunity, 1–2:307–311 (Tagliabue et al., ed. 1986).

McPheat et al., "Phase I and phase IV strains of *Bordetella pertussis* Carry a repeated DNA sequence not found in other *Bordetella* species," FEMS Microbiol. Lett. 41:357–360 (1987).

McPheat et al., "Isolation of a Repeated DNA Sequence from *Bordetella pertussis*," J. Gen. Microbiol. 133:323–330 (1987).

Park et al., "A highly conserved 530 base–pair repeated DNA sequence specific for *Bordetella pertussis*," FEMS Microbiol. Lett. 52:19–24 (1988).

Schareck et al., "Cloning of *Bordetella pertussis* Outer Membrane Proteins in *Escherichia coli*," J. Bacteriol. 159(2):780–782 (1984).

Stern et al., "Repetitive Extragenic Palindromic Sequences: A Major Component of the Bacterial Genome," Cell 37:1015–1026 (1984).

*Primary Examiner*—James Ketter
*Attorney, Agent, or Firm*—Finnegan, Henderson, Farabow, Garrett & Dunner, L.L.P.

[57] ABSTRACT

A test kit for the identification of various bacterial species groupings comprises a DNA probe which can identify palindromic units specific to particular bacterial species or species groupings. Such probes are highly specific for particular species or species subgroups. Accordingly, specific identification of bacteria may be achieved.

4 Claims, 5 Drawing Sheets

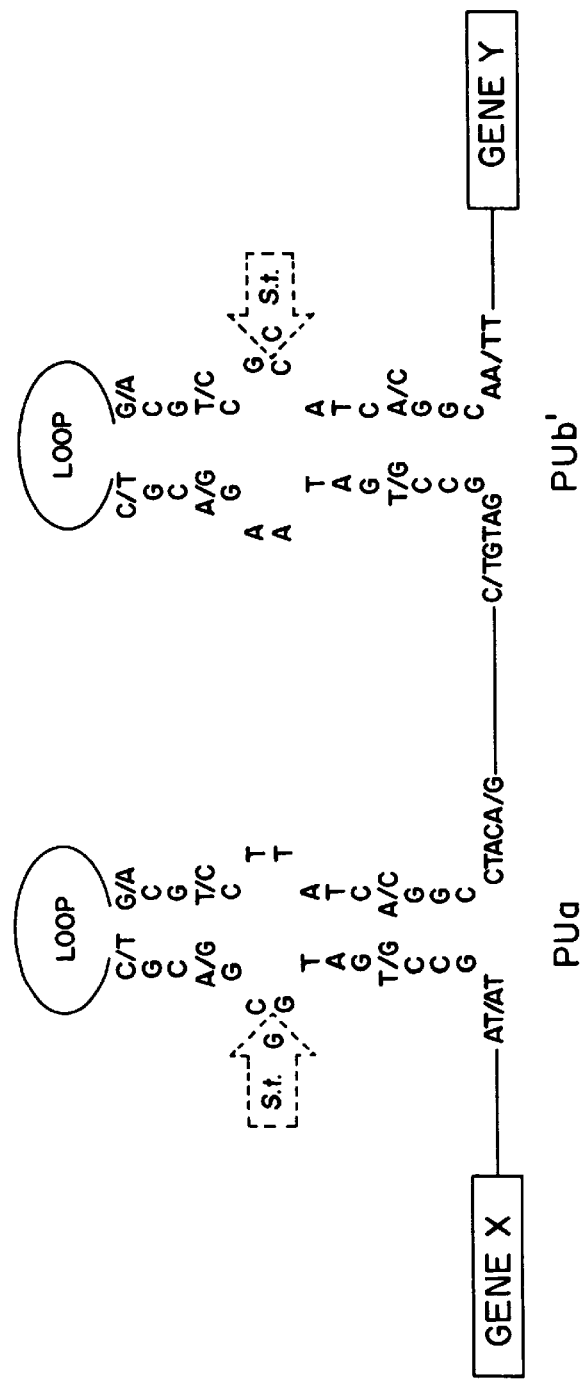
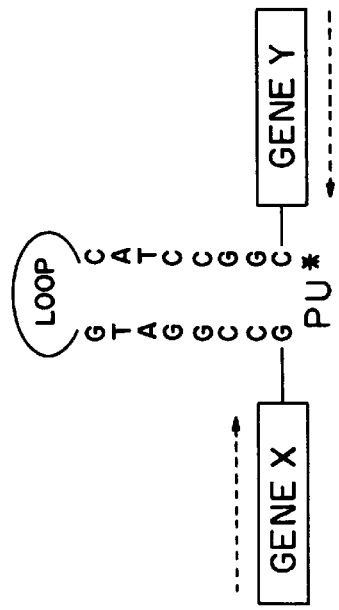
FIG. 1A
FIG. 1B

*E. coli* PU CONSENSUS

ANT GCCMGATG C GPCGC [0, 5] GCGYC T TATCEGGC CTACP

*S. typhimurium* PU CONSENSUS and SEQUENCES

| | GCCMGATGG | C | GPCGC | [0, 5] | GCGYC | T | TATCEGGC | CTACP |
|---|---|---|---|---|---|---|---|---|
| hisJa | GCCTGATGG | | CGC | tgt | GCG | | TgTCAGGC | CTACG |
| hisJb | GCCGGATGG | C | GGC | tgt | GCC | | TTgcCCGGC | CTACG |
| hisGb | GCCGGATGG | | CGC | t | GCGC | | TTATCAGGC | CTACG |
| araAa | GCCcGGTGG | C | AC | t | GCGT | | TTAcCgGGC | CTACG |
| araAb | GCCGGATGG | C | GAC | ataat | GCC | | TTATtCGGC | CTACA |
| araAc | GCCGGATGG | C | GC | tt | CGC | | TTATCCGGC | CTACG |
| alra | GCCGGgTGG | C | GC | tt | GCGC | | TTATCCGGC | CTACG |
| ushA*a | GCCTGATGG | C | GCGC | aa | CC | | TT aAGGC | tTgtA CTACG |
| ushA*b | GCCGGATaG | C | GGCGC | ttt | CGCC | | TTATCCGGC | CTACA |
| [gdhAa | GCCTGATGG | C | GC | ta | CGC | | TTATCAGGC | CTACA] |

FIG. 4

```
CTGGGACGTATCCAGCGCCCTGGCCACCGGGTCACGGGCAACCGACGCGATACCGTTGAGGGGCCGGCTGGGACTTCGT
CTTCGTGGCCATCGATGACCACGCGCGTGGCCTTCACCGACATCCACCCCGACGAGCGCTTCCCCAGCGCGCCGTCCAG
TCCTCAAGGACGCAGTGGCCTACTACCAGCGCCTGGGCGTGACCATCCAGCGCTTGCTCACCGACAATGGCTCGGCCTTT
CGCAGCCGGCCTTCGCCGCGCTGTGCCATGAG

CTGGGCATCAAGCACCGCTT     TACCCGACCTTACCGCCCAC      AGACCAATGGCAAGGCCGAA
CGCTTCATCCAGTCGGCCTT     GCGTGAGTGGGCTTACGCTC      ACACCTACCAGAACTCCCAA
CACCGAGCCGATGCCATGAA     ATCCTGGCTACACCACTACA      ACTGGCATCGACCCCACCAAG
GCATCGGGCGCGCTGTACCC     ATCTCCAGACTCAACCTGGA      CGAATACAACCTATTGACAG
TTCACAG

CTGGGACGTATCCAGCGCCCTGGCCACCGGGTCACGGGCAACCGACGCGATACCGTTGAGGGGCCGGCTGGGACTTCGT
CTTCGTGGCCATCGATGACCACGCGCGTGGCCTTCACCGACATCCACCCCGACGAGCGCTTCCCCAGCGCGCCGTCCAGT
TCCTCAAGGACGCAGTGGCCTACTACCAGCGCCTGGGCGTGACCATCCAGCGCTTGCTCACCGACAATGGCTCGGCCTTT
CGCAGCCGGCCTTCGCCGCGCTGTGCCATGAG

CTGGGCATCAAGCACCGCTT     TACCCGACCTTACCGCCCAC      AGACCAATGGCAAGGCCGAA
CGCTTCATCCAGTCGGCCTT     GCGTGAGTGGGCTTACGCTC      ACACCTACCAGAACTCCCAA
CACCGAGCCGATGCCATGAA     ATCCTGGCTACACCACTACA      ACTGGCATCGACCCCACCAAG
GCATCGGGCGCGCTGTACCC     ATCTCCAGACTCAACCTGGA      CGAATACAACCTATTGACAG
TTCACAG
```

FIG. 5

BACTERIAL DIAGNOSTIC PROBE

This is a continuation of application Ser. No. 08/164,769, filed Dec. 10, 1993, now U.S. Pat. No. 5,492,811 which is a continuation of Ser. No. 07/984,289 filed Dec. 1, 1992, now abandoned, which is a continuation of Ser. No. 07/870,234 filed Apr. 20, 1992, now abandoned, which is a continuation of Ser. No. 07/602,914 filed Oct. 24, 1990, now abandoned, which is a continuation of Ser. No. 07/085,178 filed Aug. 14, 1987, now abandoned.

BACKGROUND OF THE INVENTION

1. Field of the Invention

This invention relates to a diagnostic probe for bacteria based upon high specific nucleotidic repeat sequences, and more specifically to diagnostic test kits for this purpose.

2. Background

In 1982, the present inventors described, for the first time, a DNA sequence (30–40 bp long), which is highly repeated in the genome of *Escherichia coli* and *Salmonella typhimurium* (about 1000 times) (Higgins, C. F., Ferro-Luzzi Ames, G., Barnes, W. M Clement, J. M. and Hofnung M. (1982) Nature. 298, 760–762). These sequences are referred to as a Palindromic Unit or PU. Their primary sequence conservation is 80%.

Since then, a small difference was noticed in the PU consensus sequences between *Escherichia coli* and *Salmonella typhimurium*. This difference is an additional guanine residue in the Salmonella PU sequences. This was a preliminary indication that the PU sequences exhibit species-specificity.

Only a few families of highly repetitive DNA sequences have been described so far in bacteria. Like PUs, they display a tight species specificity. By hybridization, the 26-bp repetitive sequence family of *Neisseria spp.* (at least 20 copies per genome) was not found in various other gram-negative bacteria (Correia, F. F., Inouye, S. and Inouye, M. (1986) J. of Bacteriol. 167, 1009–1015). A repetitive DNA sequence family from *Bordetella pertussis* also appears to be species-specific (Macpheat, W. L. and MacNally, T. (1987) FEMS Lett. 41, 357–360).

Recently, hybridization experiments with *Escherichia coli* PU DNA as a probe showed that only DNA from enterobacteriaceae close to *E. coli* hybridized with good efficiency. These experiments will be mentioned, as unpublished data, in a review in Trends in Genetics. Such research allowed the present inventors to determine that the PU specificity could be used for the detection and the identification of bacteria with DNA probes corresponding to PU sequences.

From the above observations concerning enterobacteriaceae and *bordetella pertussis* repeated sequences, it appears that the presence of species-specific highly repetive DNA sequences is a general phenomenon among bacteria. Thus, the present invention relates to the use of species specific highly repetitive sequences as specific diagnostic probes. These type of bacteria probes should provide diagnostic assays which are more sensitive than assays with probes corresponding to low copy number genes.

SUMMARY OF THE INVENTION

It is an object of the present invention to provide a method for identifying bacteria in a sample from biological fluids or other sources. The method requires the preparation by appropriate and conventional techniques of bacteria capable of hybridizing with a labelled DNA probe, and a DNA probe containing a highly specific bacterial nucleotidic repeat sequence. Reagents appropriate for and conventionally utilized in such hybridization protocols are intended for use in the present invention. The claimed method requires the exposure of a bacterial sample to the DNA probe for a time period sufficient to allow hybridization of the probe to the native DNA of the sample bacteria. Conventional and appropriate washing steps remove unbound but labelled probe form the reaction vessel. Finally, conventional techniques to analyze the extent of hybridization permit a qualitative as well as quantitative identification of the sample bacteria.

In another aspect, the present invention relates to a diagnostic test kit for identifying bacteria in a sample which utilizes the labelled DNA probe containing a highly specific bacterial nucleotidic repeat sequence and appropriate reagents for allowing hybridization of the probe to the sample bacteria. A conventional and appropriate hybridization vessel is also required in which the hybridization can occur, along with appropriate and conventional post-hybridization washing reagents. The extent of hybridization is accomplished by means appropriate and conventionally utilized for this purpose.

Additional objects and advantages of the invention will be set forth in part in the description which follows, and in part will be obvious from the description or maybe learned from practice of the invention. These objects and advantages may be realized and attained by means of the instrumentalities and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWING FIGURES

FIG. 1 illustrates the palindromic unit consensus from *E. coli* (FIG. 1A) and from *S. typhimurium* (FIG. 1B).

Figures 3A, 3B:
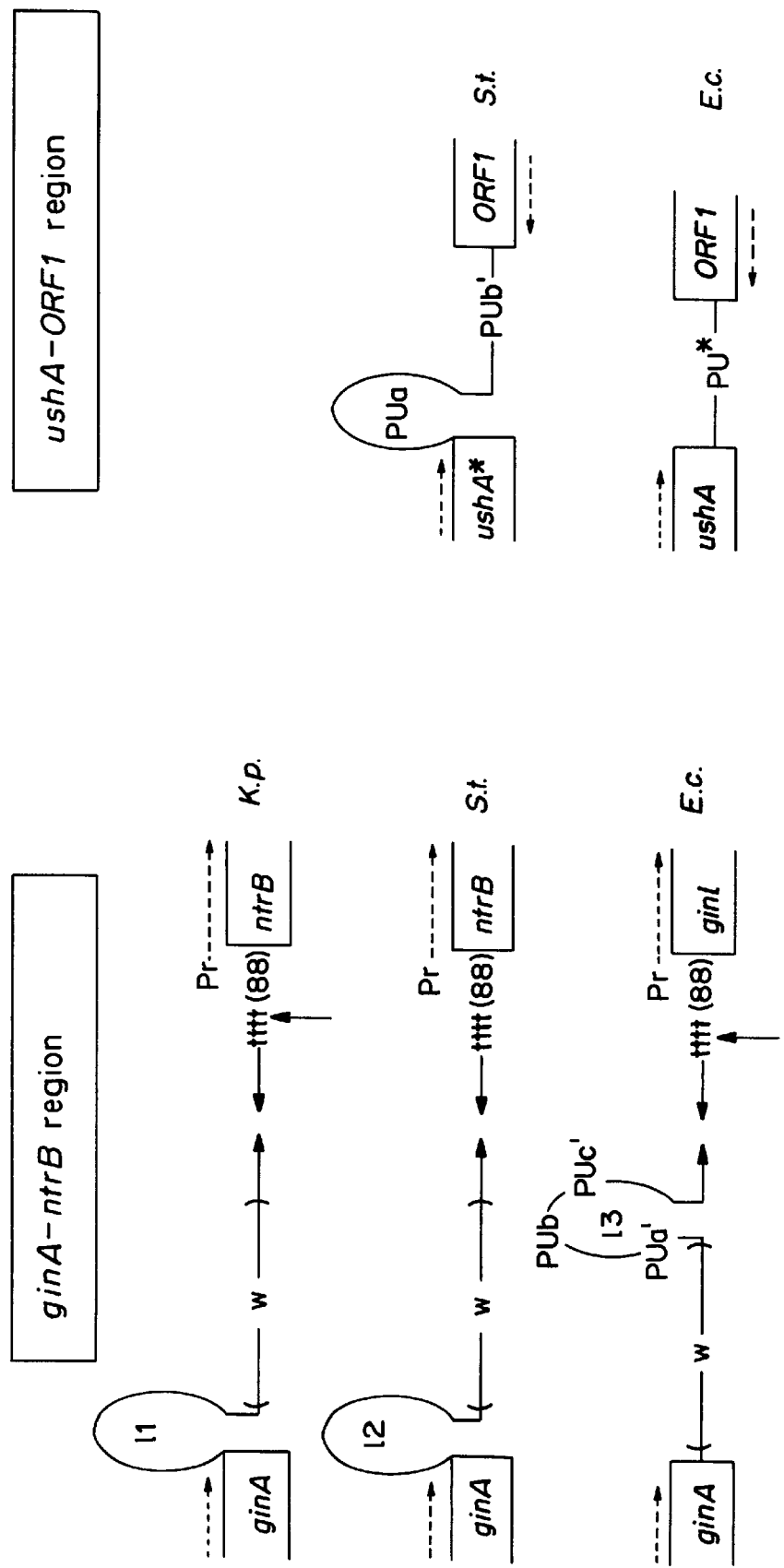

FIGS. 3(*a*) and 3(*b*) present a comparison of the structure of the 3' flanking region of the glnA gene in *Klebsiella pneumoniae*, *S. typhimurium* and *E. coli* (FIG. 3A) and of the ushA gene in *S. typhimurium* and *E. coli* (FIG. 3B).

FIG. 4 further illustrates the PU sequence consensus between *E. coli* and *S. typhimurium*.

FIG. 5 illustrates bordetella pertussis sequence information.

DETAILED DESCRIPTION OF THE PREFERRED EMBODIMENTS

Reference will now be made in detail to the presently preferred embodiments of the invention, which, together with the following examples, serve to explain the principles of the invention.

DNA sequence analysis of *E. coli* and *Salmonella typhimurium* genomes has revealed the presence of a family of highly repeated DNA sequences: the palindromic unit (PU) family. This discovery was unexpected, since prokaryotic genomes are generally small and are believed to comprise only low-copy number DNA sequences. Britten, R. J. and Kohne, D. E. (1968) Science 161, 529–560. There may by on the order of $10^3$ copies of PU sequences in *E. coli* DNA, accounting for 1% of the genome, a percentage that is comparable to values found for many families of repetitive DNA in eukaryotic genomes.

Structure and Genomic Localization of PU Sequences

Figure 2:
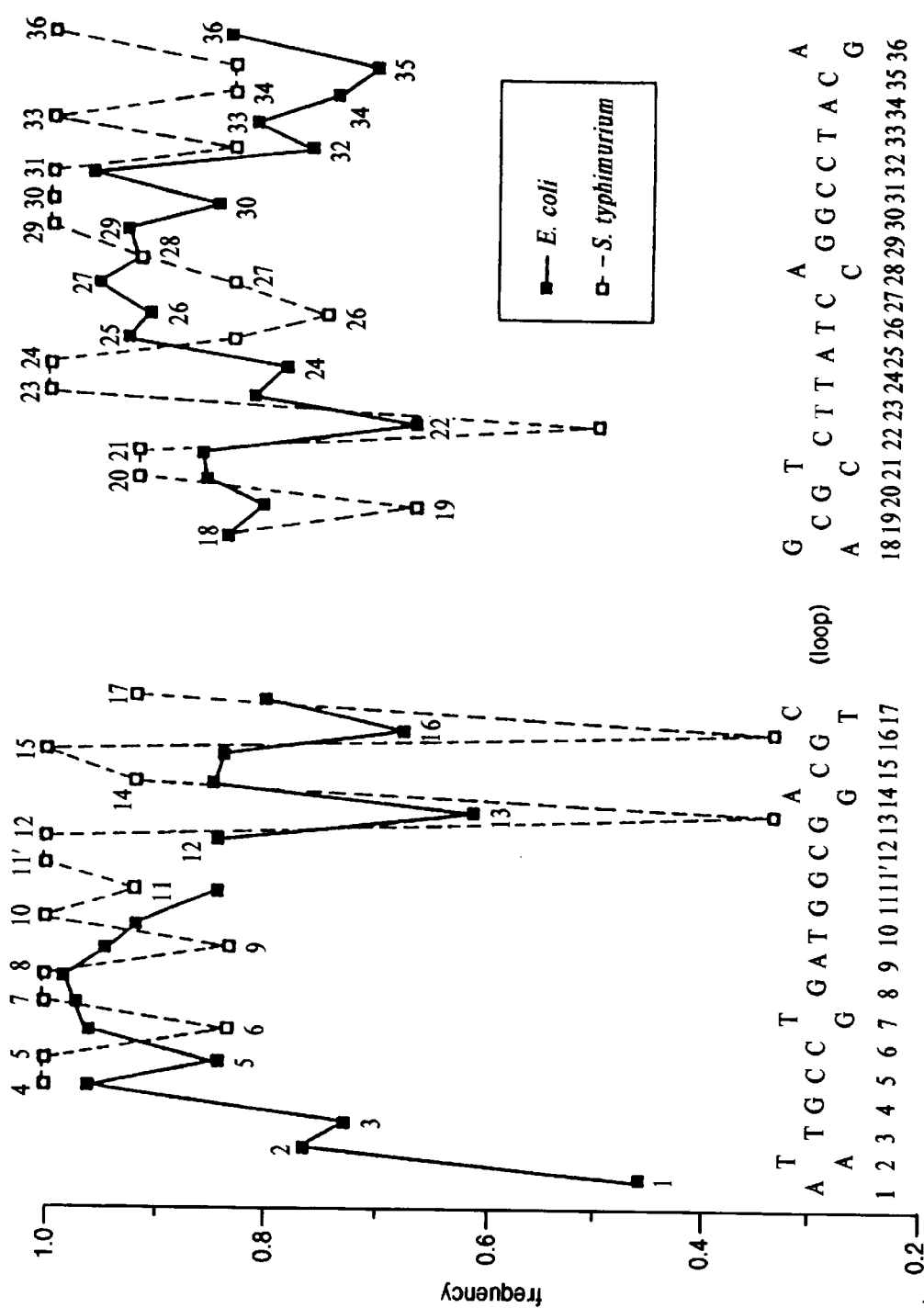
FIG. 2 illustrates the conservation of primary structures of *E. coli* and *S. typhimurium* PU sequences.

Palindromic units constitute a family of repetitive sequences of 20–40 nucleotides that exhibit dyad symmetry. A consensus has been determined from 118 different occurrences of PU sequences in the *E. coli* strain K12 (Gilson, E., Clement, J. M., Brutlag, D. and Hofnung, M. (1984) EMBO J. 3, 1417–1421) (FIG. 1). Although PUs could correspond to stable stem and loop RNA or DNA structures, the formation of such structures remains to be established. The 'stem' is GC-rich and highly conserved; it has a lower part of five base pairs. The two parts are separated by an 'internal' mismatch. The 'loop', which is AT-rich, is variable in sequence and ranges in length from 0 to 5 nucleotides. The PU stem flanking regions are highly conserved and have been called the 'external' mismatch (FIGS. 1 and 2). The internal and external mismatches constitute asymmetry elements which confer a polarity to the PU (FIG. 1).

Palindromic units are present at least several hundred times on the *E. coli* and *S. typhimurium* chromosomes, always in extragenic positions. This is why PUs are also sometimes called REP (repetitive extragenic palindromic) sequences; however, the term REP may be confusing since it is already widely used to designate plasmid regions necessary for unit-copy replication.

Palindromic units are found either between two genes of the same operon (intercistronic PUs), or after the last gene of an operon (postcistronic PUs). They are found as isolated occurrences but also occur as clusters of up to four elements. The organization of the clusters is quite remarkable: successive PUs rigorously alternative in orientation (FIG. 1). In addition, the fourth position of the stem which can be, with similar frequencies, either G or T, also alternates. This suggests the existence of a very specific mechanism for the generation or selection of the clusters.

The homogeneity (the number of bases identical to the consensus divided by the total number of bases) is extremely high, averaging 80% (FIG. 2). A change in one of the more conserved positions in the branch of the stem is often accompanied by a simultaneous change of the corresponding position in the other branch, so that the complementarity between these two positions is maintained. Possible reasons for the remarkable conservation in sequence and symmetry are discussed later.

FIG. 1 shows the consensus sequence from the 12 known *S. typhimurium* PU sequences that are available (Newbury, S. F. et al. (1987) Cell 48, 297–310). This sequence is similar to the *E. coli* consensus except for a highly conserved additional G before the C of the internal mismatch. The significance of this slight difference in the consensus of the two species is discussed in a later section.

When an *E. coli* PU DNA was used as a probe, only DNA from enterobacteriaceae closely related to *E. coli* showed appreciable hybridization. By computer search, the present inventors were unable to detect a palindromic-sequence family (of any primary sequence) in the *Bacillus subtilis* sequence database. There are a number of possible explanations for this: (1) there may be biases in the *B. subtilis* sequence databases; (2) in *B. subtilis* the functional equivalent of the enterobacteriaceae PU family may not be a palindromic sequence; (3) there may be no functional equivalent of PUs in *B. subtilis*. The same search in *E. coli* revealed PU as the only highly repetitive palindromic DNA sequence in this bacterium. Saurin, W. Cabios 3, 121–127. It should be noted that PU sequences were not found in the complete genome of lambda or T7 phages. Finally, neither the PU consensus nor variations with up to four differences in one of each 'half-PU' (i.e. positions 1–17 and positions 18–36 on FIG. 2) are found in the eukaryotic sequence database.

All this suggests that PU sequences are characteristic of the chromosomes of certain enterobacteriaceae. Because sequence data for most bacterial species are still poorly represented in databases, we have not ruled out the possibility that highly repetitive palindromic elements with sequences different from PU may exist in other bacterial species.

The localization of PU clusters is conserved between the genomes of different isolates of the *E. coli* K12 strain. This reveals that PUs are stable or at least do not constitute very unstable genetic elements. PUs are not necessarily present in the same position in otherwise highly homologous sequences of DNA of *E. coli* and *S. typhimurium* (FIG. 3). Thus, like the PU primary sequences, the PU genomic localizations are characteristic of bacterial species.

PUs and mRNA

Most PUs do not act as transcription terminators. The two PUs located between the cotranscribed genes hisJ and hisQ of the histidine transport operon in *S. typhimurium* do not cause transcription termination in vivo (less than 50% transcription arrest in a galK fusion analysis system). No pause or termination of transcription was detected in vitro. Stern, J. M. et al. (1984) Cell 37, 1015–1026. The three PUs located between the cotranscribed genes lamB and malM of the maltose transport operon in *E. coli* did not affect the transcription and translation of a down-stream gene (galK gene in a multicopy system and lacZ gene in a monocopy system). Gilson, E., Rousset, J. P., Clement, J. M. and Hofnung, M. (1986) Ann. Microbiol. (Inst. Pasteur) 127B,, 259–270. For several *E. coli* operons, the major messenger endpoint was mapped at a typical factor-independent transcription termination or located next to, but clearly distinct from, PU. Gilson, E., Rousset, J. P., Clement, J. M. and Hofnung, M. (1986) Ann. Microbiol. (Inst. Pasteur) 127B, 259–270.

However, some PUs do terminate transcription. The single postcistronic PU located between the pheA gene and the tyrA gene acts as a bidirectional transcription terminator. From the sequence of this PU we can define a subclass of PU called PU* (FIG. 1). Interestingly, the six known PU* sequences are each located between two convergent open reading frames, and account for most of the DNA in these regions. No other obvious transcription terminator sequence exist in their vicinity, leaving open the possibility that they all have this function.

A comparison of the expression of a region that is highly homologous in *E. coli* and *S. typhimurium,* the ushA-ORF1 region, is compatible with the idea that PU* sequences act as bidirectional transcription terminators. The two genes are convergently transcribed and separated by a PU* sequence in *E. coli* and by a cluster of two classical PUs in *S. typhimurium* (FIG. 3). A protein corresponding to ORF1 is expressed at a high level in both species. However, the ushA protein from *S. typhimurium* is much less strongly expressed than the corresponding *E. coli* ushA protein. Remarkably, genetic inactivation of ORF1 transcription results in increased expression of ushA°. Burns, D. M. and beacham, I. R. (1986) J. Mol. Biol. 192, 163–175. One possibility is thus that ORF1 transcription inhibits ushA° expression in *S. typhimurium*, but not ushA expression in *E. coli* thanks to transcription arrest by the PU*.

A termination site, presumed to be rho-dependent, has been mapped between the two PU located after the A gene. Spencer, M. E. and Guest, J. R. (1985) Mol. Gen. Genet. 200, 145–154. It may be significant that the CAA-CA sequence located between these two PUs is also found near the end of several rho-dependent terminators: Pr, P1, tRNA$^{tyr}$ and trpt'. Morgan, W. P., Bear, D. G., Litchman, B. L. and von Hippel, P. H. (1985) Nucleic Acids Res. 13, 3739–3754.

Certain PUs have a limited effect on gene expression, through stabilization of the 3' end of the mRNA. A deletion of the two intercistronic PUs between hisJ and hisQ does not affect the expression of the distal part of the operon but leads to a two-fold decrease of the expression of the upstream gene, hisJ. A similar observation was made by Plamann et al. with the post-cistronic PU of the glyA operon: a mu phage insertion located between the translation stop codon and the first PU was responsible for three-fold decrease in expression of the upstream glyA gene. Plamann, M. D. and Stauffer, G. V. (1985) J. Bacteriol. 161, 650–654. Recently, it has been shown in two cases that this increase in expression of the upstream gene is a consequence of the accumulation of upstream mRNA species. This observation was explained by the ability of the PU sequence to protect the transcript from 3'–5' exonuclease degradation.

It is now well established that a number of sequences able to form RNA secondary structures can function as barriers against 3'–5' exonuclease digestion. Therefore, it is not surprising that PU sequences, which have the potential to form stable stem and loop structures at the level of mRNA, may exhibit such an activity.

One PU of the rplL-rpoB region includes an RNaseIII processing site. The sequence of this PU is atypical: the upper part of the stem and the loop are missing. Interestingly, some loose homology exists between the lower part of the stem and a known RNAaseIII site in phage T7. Gilson, E., Clement, J. M., Brutlag, D. and Hofnung, M. (1984) EMBO J. 3, 1417–1421. No other evidence exists in association of a PU with RNaseIII processing. In particular, the two typical PUs in the hisJ-hisQ region are not processed by RNaseIII In vitro. The above examples strongly suggest that slight sequence modifications from the PU consensus sequence or modification of the PU sequence environment can have various effects on the transcription of specific operons. The selective advantage conferred to the cell by these functional modifications of PU would tend to increase differences between PU sequences. However, since all these structures are still recognizable as PUs, there probably exist some mechanisms for the maintenance of homogeneity amongst PU sequences within a species.

PUs and Chromosomal Organization

The existence and the intergenic location of such a large number of homologous sequences suggest that they could be associated with chromosome rearrangements (gene shuffling). The remarkable conservation of the PU primary sequence and its dyad symmetry (reminiscent of sites for restriction enzymes) suggest that PU DNA may constitute protein binding sites.

It is unlikely that PUs are major sites for high frequency recombination for the two following reasons: (1) two clusters of PU, separated by about 3 kpb, are found in the malB region of *E. coli*—however, no Mal$^-$ deletion mutant has ever been found that has an end-point in the malB PU regions; and (2) most of the spontaneous tandem duplications in *S. typhimurium* arise by unequal recombination between rrn operons.

However, a PU-mediated low frequency recombinational activity, like that promoted by any repeated sequence, could very well occur. Even under such conditions, PUs could play a role in chromosome rearrangements and in the modular evolution of genomes. In support of this idea, one arrangement has been detected in *S. typhimurium* between the hisG-hisD intergenic region, which contains one PU, and argB. Anderson, P. and Roth, J. (1978) J. Mol. Biol. 119, 147–166. Moreover, one PU is at the boundary between homologous and non-homologous regions of at least one rrn operon in *E. coli*, one PU constitutes the exact boundary between homologous and non-homologous region of glnA between *E. coli* and *S. typhimurium* (FIG. 3), and PU sequences are present exactly at the boundary of directly repeated sequences located after the M1 RNA gene and after the tRNA$^{Pro}$ gene. Reed, R. E. and Altman, S. (1983) Proc. Nat'l. Acad. Sci. USA 80, 5359–5363; Kuchino, Y., Mori, F. and Nishimura, S. (1985) Nucleic Acids Res. 13, 3213–3220. Although the evidence is indirect, these observations are consistent with the occurrence of recombinational events close to the PU sites.

In the presence of an extract containing nucleoid-associated proteins, PU sequences constitute a strong boundary to ExoIII digestion. Gilson, E. et al. (1986) FEBS Lett. 206, 323–328. A single PU, in either orientation, is sufficient to stop degradation. These findings are consistent with the idea that one or several nucleoid-associated proteins are able to recognize and bind PU sequences.

The biological significance of this interaction is not known. It would be consistent with an involvement of PUs in the structure of the nucleotoid. Recent studies on eukaryotic chromatin structure have implicated the topoisomerasell protein in the organization of the DNA into looped domains, via interaction with specific DNA sequences. On the basis of electron microscopy studies and of in-vivo supercoiling distribution measurements, it appears that the *E. coli* nucleoid is folded into independent supercoiled looped domains. It is possible that clamping two PU clusters by specific protein interactions would constitute and/or stabilize the neck of each loop.

PUs and the Molecular Definition of Bacterial Species

The high copy number of PUs suggests that an efficient mechanism for spreading has been involved. Several mechanisms have been described in eukaryotes, including retroposition (i.e. reverse transcription of an RNA, often a tRNA), gene conversion, unequal recombination, slippage replication, transposition and amplification from a progenitor repeat. Dover, G. A. (1986) Trends Genet. 2, 159–165. None of these mechanisms can be excluded here. However, PUs do have features in common with some transposons, including their inverted repeat structure (reminiscent of IS), and partial homologies between the PU stem consensus sequence and the ends of transposons.

The high degree of homogeneity of PUs can be explained by at least two hypotheses: (1) that they have arisen recently and spread rapidly (for example by transposition); (2) that they are of more ancient origin, and that there exists a specific mechanism for maintaining homogeneity. Since both *E. coli* and *S. typhimurium* possess PUs and, in some cases, they are at the same genetic location (e.g. the ushA region) it seems that PU formation occurred before these two species diverged. This argues against the first hypothesis. The slight difference in their consensus sequences suggests that the homogeneity of PU sequences within one species is higher than between two different species, and implies species-specific mechanisms for the maintenance of the homogeneity. Such a pattern of variation within a sequence family, called concerted evolution,, has already been observed in many eukaryotic families such as rDNA, small nuclear (sn) RNA or long interspersed repetitive DNA sequences (LINE). It is possible that the existence of a protein binding to PU sequences (see above) might lead to slow coadaptative changes between the PU sequences and the gene of the relative protein. This would tend to lead to the homogenization of the PU family within a species.

Like the PUs, three other known families of repetitive DNA sequences in bacteria display a tight species specificity. No sequences hybridizing with the 26-bp repetitive sequence family of *Neisseria spp.* (at least 20 copies per genome and possibly many more) have been found in various other Gram-negative bacteria. Correia, F. F., Inouye, S. and Inouye, M. (1986) J. Bacteriol. 167, 1009–1015. The nifHDK promoter sequence, which is repeated 3–6 times on the symbiotic plasmid of *Rhizobium trifolii* does not hybridize to DNA of any other symbiotic plasmid-containing Rhizobium species examined. Watson, J. M. and Shofield P. R. (1985) Mol. Gen. Genet. 199, 279–289. The 11-bp repeat of Haemophilus ($10^3$ copies per genome) allows specific recognition of Haemophilus DNA to be taken up by competent cells. Danner, D. B., Deich, R. A. Sisco, K. L., Deich, R. A., Sisco, K. L. and Smith, H. O. (1980) Gene 11, 311–318. In addition, a repetitive DNA sequence family has been found recently in *Bordetella pertussis*. Once again, this sequence seems to be species-specific. MacPheat, W. L. and MacNally, T. (1987) FEMS Lett. 41, 357–360 and A. Ullmann, pers. communication).

A stimulating aspect of the discovery of bacterial repetitive sequences is that many of the exciting hypotheses and speculations stemming from the discovery of these structures in eukaryotes are now within experimental reach in genetically well characterized organisms such as *E. coli*. Clues to the origin and function of such sequences may be forthcoming in the near future.

It is understood that the application of the teachings of the present invention to a specific problem or environment will be within the capabilities of one having ordinary skill in the art in light of the teachings contained herein. Examples of the products of the present invention and representative processes for their isolation and manufacture appear in the following examples.

EXAMPLES

Example I

Evidence of differences in PU between otherwise homologous bacterial DNA sequences.
1. Three genetic regions which are otherwise highly homologous between *Escherichia coli* and *Salmonella typhimurium* do not contain PU at identical positions (Newbury et al., 1986; Gilson et al., in preparation).

The region between the stop codon of glnA and the transcription terminator contains three PU in *Escherichia coli* and none in the equivalent region of *Salmonella typhimurium* and *Klebsiella pneumoniae* (Mac Farlane and Merrick, 1985).

Two PU are located 20 bp after the stop codon of the metJ gene of *Escherichia coli*. The equivalent region of *Salmonella typhimurium* does not contain any PU but contains a typical factor-independent termination site (Saint-Girons et al., 1984) (Urbanowski and Stauffer, 1985). Available sequence data does not allow to define the right boundary of the PU containing insert in *Escherichia coli*.

A single PU is located between the end of gene rpoD and a functional factor region of *Salmonella typhimurium,* only a portion of this PU is present (Erickson et al., 1985).

The malE-malF intergenic region (Duplay et al., 1984 and Duplay, personal communication) (Froshauer and Beckwith, 1984), the 3' flanking region of uvrD (Finch and Emmerson, 1984) (Yamamoto et al., 1986) have been cloned and sequenced from different *Escherichia coli* sources, in different laboratories. In the three cases, the region contains identical PU sequences.

Thus, PU localization appears to be conserved between different strains of *Escherichia coli* while it is not conserved between *Escherichia coli* and *Salmonella typhimurium*. Thus, PU localization seems to be a characteristic of bacterial species.

2. Available PU sequences from *Escherichia coli* and *Salmonella typhimurium*.

The 9 known *Salmonella typhimurium* PU sequences that are available, all comprise an additional G before the C of the C-T "mismatch" (FIG. 4). Since amonth the 103 *Escherichia coli* PU sequences recorded in our laboratory, only one (gdhA, PUa) contains the additional G, we propose that the PU consensus may be slightly different in *Escherichia coli* and *Salmonella typhimurium* (the modified *Salmonella typhimurium* PU consensus is shown on FIG. 4). That these two related enterobacteriaceae present this slight difference in their PU sequences suggests that the primary sequence of PU could be specific of one or a group of bacterial species. In addition, it should be recalled that PU sequences are not present in the complete genome of lambda or T7 phages (Gilson et al., 1984).

3. Existence of sequences in prokaryotic species more distant from *Escherichia coli*.

The TGV program (Saurin and Marliere, 1987) was used to search a *Bacillus subtilis* sequence database (29417 b.p. for 33 sequences, extracted from Genbank release 38, November 1985). This program allows to look for repetitive DNA pattern irrespective of their primary sequences. Parameters required that repetitive DNA patterns consecutives bases, all the bases of the stem being paired using Watson-Crick and complementary rules (i.e. A-T or G-C pairing). This search revealed no family of repetitive palindromic sequences in the *Bacillus subtilis* sequence database. Indeed, we found only one palindromic sequence having more than two occurences. This sequence, CCACCTTGCCAAGGTGG, corresponds to the anticodon stem and loop of Gly-tRNA which is encoded by three different genetic regions: trrnB (Wawrousek and Hansen, 1983), trrnD (Wawrousek et al., 1984) and trrnE (Green and Vold, 1983; Wawrousek et al., 1984). Although the *Bacillus subtilis* sequence database contains about ten fold less sequences than the *Escherichia coli* one, if "PU like" sequence were present at the same frequency in the two species, one would expect to find about 10 occurences in *Bacillus subtilis*. It should be noted that the same search in *Escherichia coli* revealed PU as the only highly repetitive palindromic sequence in this bacteria (Saurin, 1987).

4. Analysis.

All the three points presented above suggest that PU contribute to bacterial speciation. Many different modes for direct or indirect effects can be imagined. One hypothesis we like to consider is that PU might play a role in the bacterial chromosome structure. This could prevent stable or viable insertion of a large segment of a foreign chromosome, not containing PU. Preliminary results show that a chromoid-associated protein specifically interacts with PU DDNA (Gilson et al., 1986a). This is compatible with the idea that PU sequences can be involved in the structure of the chromosome.

Example II

Analysis of hybridization utilizing *E. coli* labelled probe. We examined 100 DNA of different bacterial species either by dot blot or by southern blot with a 200 bp DNA probe containing 3 PU sequences. The hybridization experiments have been performed using standard procedures with the following modifications: hybridization step in 6 SSC, 0.1% SDS at 58° C., 12 hours and washing in 0.2 SSCC, 0.1% SDS at 45° C., 1 hour. The probe as been prepared by nick translation with alpha $^{32}$p nucleotides. The 100 bacterial species included a representative set of *enterobacteria* (85 different species) and a set of other bacteria which is composed of 3 different Xenorhabdus species, Acinetobacter, *Bordetella bronchisepta*, *Pseudomonas aeruginosa*, Aeromonas, Actinobacillus, Pasteurella, *Vibrio cholerae, Vibrio mimicus, Legionella pneumophila, Bacillus subtilis,* Calothrix and Methanococcus.

Following the foregoing analysis, our results indicated that only the *E. coli* and Salmonellae groups hybridize with such a probe under the hybridization conditions specified.

Example III

Hybridization specificity of bordetella sequences.

Following the general procedure of Example I, hybridization experiments were conducted with a 240 base pair sequence units extracted from *Bordetella pertussis*. Modification of the conventional hybridization protocol step utilized 50% formamide at 42° C. for a 12 hour incubation and washing at 65° C. with 0.1 SSC and 0.1% SDS. Additional hybridizations were performed in slightly less stringent conditions with 2 SCC and 0.1% SDS. The *B. pertussis* sequence did not hybridize with *B. para pertussis* nor with *B. avium* or *B. bronchoseptica*.

Example IV

Utilization of alternative conventional labels.

Hybridization experiments as in Examples I and II are performed with labelled probes. Conventional labelling techniques involving conventional radioactive, immunoenzymatic or immunofluorescent techniques are utilized. Results confirm the presence or absence of hybridization utilizing probe sequences and target bacteria as in Examples I and II.

It will be apparent to those skilled in the art that various modifications and variations can be made to the processes and products of the present invention. Thus, it is intended that the present invention cover the modifications and variations of this invention provided they come within the scope of the appended claims and their equivalents.

Example V

A diagnostic test kit for the in vitro identification of bacteria in a sample from biological fluids or other sources is composed of a conventional hybridization vessel into which appropriately-treated aliquots of sample material containing bacteria to be identified may be added. Labelled probe DNA may be added as a separate reagent or, alternatively, may be present when fixed by appropriate techniques.

After appropriate incubation periods have passed, hybridization is halted by washing of unlabelled probe material from the sample vessel. The presence and quantification of hybridization may be determined by measuring the amount of probe bound to the DNA of sample bacteria.

What is claimed is:

1. A method for improving the sensitivity of an assay for identifying bacteria in a sample by providing an increased number of species specific probe binding sites for said DNA of said bacteria in said sample comprising the steps of (A) exposing the sample bacteria containing native DNA to a labeled DNA probe in the presence of a reagent that allows hybridization of said probe and the native DNA of the sample bacteria to be identified,
      wherein said DNA probe contains a high copy number, repeat, nucleotide sequence specific to said bacteria, and the high copy number, repeat, nucleotide sequence provides the increased number of species specific probe binding sites; and
      wherein said repeat sequence is a member of a family of repeat sequences and said family of repeat sequences is present in more than one species of bacterium;

(B) washing non-hybridized labeled DNA probe from the sample; and (C) analyzing the extent of resultant hybridization.

2. The method of claim 1 wherein said labelled DNA probe is labelled by a technique selected from the group consisting of immunoenzymatic, radio isotopic and immunofluorescent techniques.

3. The method of claim 1, wherein the nucleotidic repeat sequence is a palindromic unit.

4. The method of claim 3, wherein said labelled DNA probe is labelled by a technique selected from the group consisting of immunoenzymatic, radioisotopic, and immunofluorescent techniques.

* * * * *